(12) United States Patent
Murphy

(10) Patent No.: US 10,603,154 B2
(45) Date of Patent: Mar. 31, 2020

(54) DEVICES AND METHODS FOR PREVENTING INCISIONAL HERNIAS

(71) Applicant: Prevent Patch, LLC, Bloomfield Hills, MI (US)

(72) Inventor: John W. Murphy, Bloomfield Hills, MI (US)

(73) Assignee: Prevent Patch, LLC, Bloomfield Hills, MI (US)

( * ) Notice: Subject to any disclaimer, the term of this patent is extended or adjusted under 35 U.S.C. 154(b) by 190 days.

(21) Appl. No.: 15/562,065

(22) PCT Filed: Feb. 15, 2016

(86) PCT No.: PCT/US2016/017952
§ 371 (c)(1),
(2) Date: Sep. 27, 2017

(87) PCT Pub. No.: WO2016/160148
PCT Pub. Date: Oct. 6, 2016

(65) Prior Publication Data
US 2018/0064522 A1    Mar. 8, 2018

Related U.S. Application Data

(63) Continuation of application No. PCT/US2015/056395, filed on Oct. 20, 2015, which
(Continued)

(51) Int. Cl.
*A61B 17/04* (2006.01)
*A61B 17/00* (2006.01)
(Continued)

(52) U.S. Cl.
CPC ........ *A61F 2/0063* (2013.01); *A61B 17/0482* (2013.01); *A61B 17/0466* (2013.01);
(Continued)

(58) Field of Classification Search
CPC ............ A61F 2/0063; A61F 2250/0097; A61F 2002/0068; A61F 2210/0004;
(Continued)

(56) References Cited

U.S. PATENT DOCUMENTS 2,012,755 A * 8/1935 De Muth ............. A61B 17/085
606/217
2,387,131 A * 10/1945 Fernandez ........... A61B 17/085
606/216
(Continued)

FOREIGN PATENT DOCUMENTS

CN       103519856 A    1/2014
EP        2305132 A1    4/2011
(Continued)

OTHER PUBLICATIONS

International Search Report and Written Opinion dated May 31, 2016, 16 pages.
International Search Report dated May 31, 2016, 15 pages.

*Primary Examiner* — Julian W Woo
(74) *Attorney, Agent, or Firm* — Gunther J. Evanina; Butzel Long

(57) ABSTRACT

A reinforcement device [10] comprises a biocompatible material such as a mesh sheet [12] for closing and reinforcing the closure of a surgical incision, including an elongated abdominal incision. The biocompatible material may provide one or more of a column of hooks [16a, 16b] or a column of apertures [31a, 31b] or markings [51a, 51b] to indicate where puncturing/suturing is to occur and/or where the device [10] is to be positioned. A disclosed ratio of suture [22] length to incision length is 4:1. The reinforcement device [10], when implanted through surgery, may reduce the likelihood of and/or prevent incisional hernias. The reinforcement device [10] may be included in a surgical kit.

11 Claims, 6 Drawing Sheets

Related U.S. Application Data is a continuation of application No. 14/674,618, filed on Mar. 31, 2015, now Pat. No. 9,895,212.

(51) Int. Cl.
*A61F 2/00* (2006.01)
*A61B 90/00* (2016.01)

(52) U.S. Cl.
CPC ............... *A61B 2017/00004* (2013.01); *A61B 2017/0495* (2013.01); *A61B 2090/061* (2016.02); *A61B 2090/0807* (2016.02); *A61F 2002/0068* (2013.01); *A61F 2210/0004* (2013.01); *A61F 2220/0083* (2013.01); *A61F 2250/0097* (2013.01)

(58) Field of Classification Search
CPC .. A61B 2017/0495; A61B 2017/00004; A61B 17/0466
See application file for complete search history.

(56) References Cited

U.S. PATENT DOCUMENTS

| | | | | |
|---|---|---|---|---|
| 3,762,255 | A * | 10/1973 | Clash | A41B 17/00 83/309 |
| 4,854,316 | A | 8/1989 | Davis | |
| 5,377,695 | A * | 1/1995 | An Haack | A61B 17/085 128/888 |
| 6,093,201 | A * | 7/2000 | Cooper | A61B 17/80 606/232 |
| 6,171,318 | B1 * | 1/2001 | Kugel | A61F 2/0063 602/44 |
| 7,105,001 | B2 * | 9/2006 | Mandelbaum | A61B 17/08 128/898 |
| 7,566,337 | B2 | 7/2009 | Sogaard-Andersen et al. | |
| 7,662,169 | B2 | 2/2010 | Wittmann | |
| 8,357,172 | B2 | 1/2013 | Harper | |
| 8,579,922 | B2 * | 11/2013 | Glick | A61B 17/06166 606/148 |
| 8,657,853 | B2 | 2/2014 | Straehnz | |
| 8,679,153 | B2 | 3/2014 | Dennis | |
| 8,759,287 | B2 | 6/2014 | Robson | |
| 8,795,384 | B2 | 8/2014 | Nelson et al. | |
| 9,308,070 | B2 * | 4/2016 | Mortarino | A61F 2/0063 |
| 9,492,171 | B2 * | 11/2016 | Patenaude | A61B 17/085 |
| 10,448,951 | B2 * | 10/2019 | Stevenson | A61B 17/08 |
| 2005/0043818 | A1 | 2/2005 | Bellon Caneiro et al. | |
| 2006/0259075 | A1 | 11/2006 | Mandelbaum | |
| 2008/0208213 | A1 * | 8/2008 | Benjamin | A61B 17/0057 606/139 |
| 2009/0192532 | A1 | 7/2009 | Spinnler et al. | |
| 2012/0232334 | A1 | 9/2012 | Bell et al. | |

FOREIGN PATENT DOCUMENTS

| | | |
|---|---|---|
| GB | 2430372 A | 3/2007 |
| WO | WO-0189392 A2 | 11/2001 |
| WO | WO-03037215 A2 | 5/2003 |
| WO | WO-2004103166 A2 | 12/2004 |
| WO | WO-2008/140439 A1 | 11/2008 |
| WO | WO-2013140259 A1 | 9/2013 |
| WO | WO-2014/048981 A1 | 4/2014 |

\* cited by examiner

DEVICES AND METHODS FOR PREVENTING INCISIONAL HERNIAS

CROSS-REFERENCE TO RELATED APPLICATIONS

This national application filed under 37 CFR § 371 claims priority to International Patent Application No. PCT/US2016/017952, filed Feb. 15, 2016, which claims priority to PCT/US2015/056395, filed Oct. 20, 2015 and U.S. patent application Ser. No. 14/674,618, filed Mar. 31, 2015.

FIELD OF THE DISCLOSURE

This disclosure relates to medical devices, kits, and methods for contemporaneously closing and reinforcing incision closures. Such devices, kits and methods reinforce closures and may reduce the likelihood of or prevent incisional hernias.

BACKGROUND OF THE DISCLOSURE

Incisional hernias are detectable defects in a surgical site following the creation of a surgical incision. Such hernias may become apparent as a palpable defect; that is, abdominal contents may protrude beyond where they should and therefore can be physically felt. In some instances, incisional hernias may present merely as a protrusion within a healed incision.

Incisional hernias following surgery are a common complication following certain surgeries, including but not limited to a laparotomy. A laparotomy is a surgical procedure involving an incision through the abdominal wall to gain access into the abdominal cavity. There are numerous reasons why a particular patient might suffer from an incisional hernia following a laparotomy or other surgery. Patients suffering from obesity, diabetes, or malnutrition may be more susceptible to an incisional hernia. A patient may have poor tissue, or an infection at the incision site, making him or her more susceptible. In other instances, a closure of an incision may not be sufficiently strong to guard against incisional hernias. An unfortunate result is that incisional hernias are not particularly rare. In fact, following a laparotomy, the incidence of incisional hernia has ranged from 15-40%.

The incidence of incisional hernias is serious. Correction usually calls for surgical intervention, re-operation, and/or prolonged hospitalization. Incisional hernias also may increase morbidity and mortality. In other words, the costs to the health care system and the patient are significant, fiscally and otherwise.

It is desirable to reduce the incidence of incisional hernias, or to prevent hernias during an initial operation, by reinforcing surgical closures using medical devices, kits and/or methods.

DETAILED DESCRIPTION

Multiple embodiments of the disclosed devices, kits and methods are described with reference to only a few exemplary drawings. Although a particular embodiment may be illustrated and described herein as including particular components in a particular configuration, such components and configuration are for exemplary purposes only. The figures and descriptions of the embodiments described herein are not intended to limit the breadth or the scope of the inventive concepts or the appended claims. Rather, the figures and detailed descriptions are provided to illustrate the inventive concepts to a person of ordinary skill in the art and to enable such person to make and use the inventive concepts.

Figure 1:
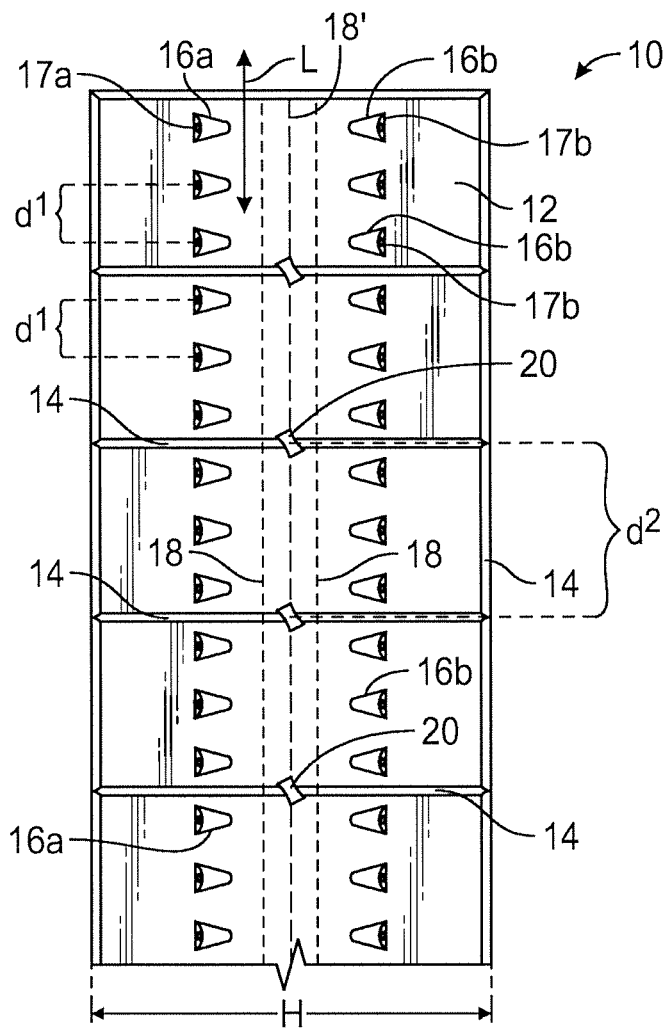
FIG. 1 is a top view of an exemplary reinforcement device.
Figure 2:
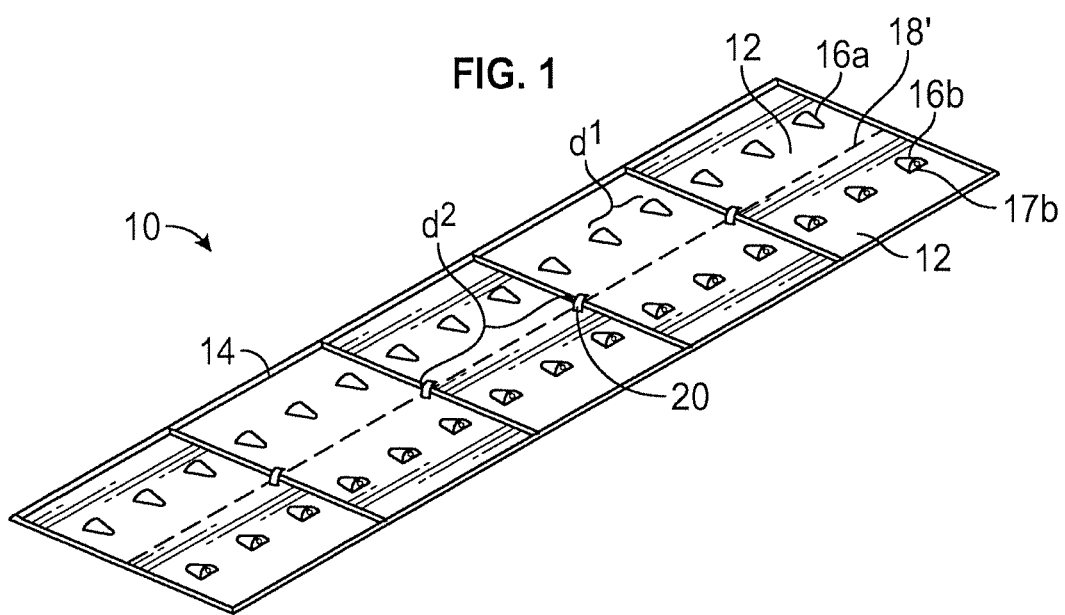
FIG. 2 is perspective view of an exemplary reinforcement device.
Figure 3:
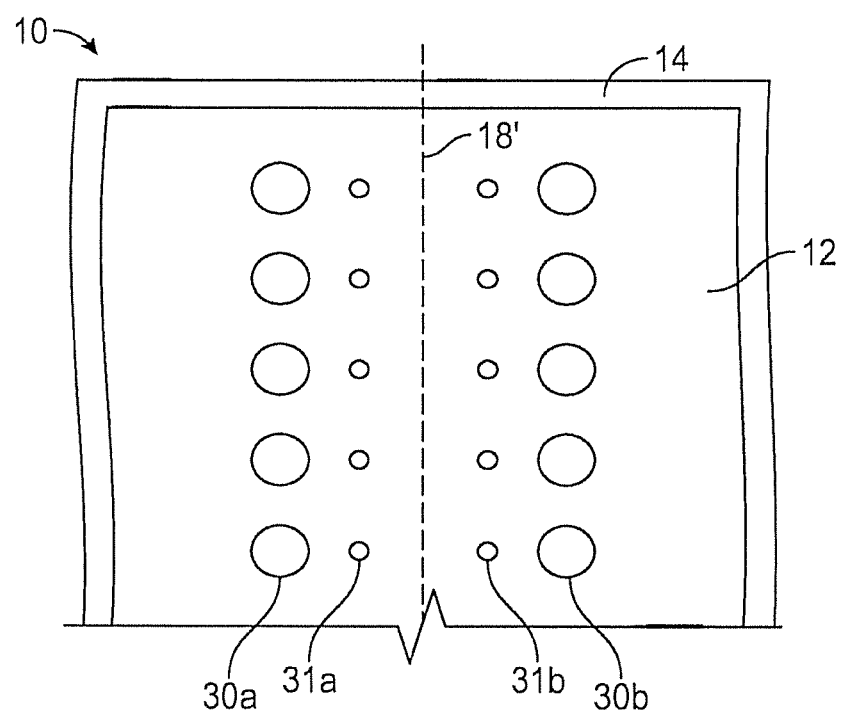
FIG. 3 is a top view of an exemplary reinforcement device.

With reference to FIGS. 1-3, exemplary reinforcement device 10 is shown. Reinforcement device 10 comprises a sheet of biocompatible material which is exemplified as mesh sheet 12. Sheet 12 is depicted as rectangular, but other shapes are contemplated. For example, there may be rounded corners on a rectangular shape. The shape should have a longitudinal axis and a latitudinal axis.

The biocompatible material may be bioabsorbable, non-bioabsorbable, partially bioabsorbable, or some combination of one or more of these. The biocompatible material may comprise any of a number of materials. By way of non-limiting examples, bioabsorbable materials may comprise polyhydroxy acids, polylactides, polyglycolides, polyhydroybutyrates, polyhydroxyvaleriates, polycaprolactones, polydioxanones, synthetic and natural oligo- and polyaminoacids, polyphosphazenes, polyanhydrides, polyorthoesters, polyphosphates, polyphosphonates, polyalcohols, polysaccharides, and polyesters. By way of non-limiting examples, mon-bioabsorbable materials may comprise polyalkenes (including but not limited to polyethylene and polypropylene), fluorinated polyolefins, polytetrafluoroethylene, polyvinylidenefluoride, polyamides, polyurethanes, polyisoprenes, polystryrenes, polysilicones, polycarbonates, polyaryletherketones, polymetacrylates, polyacrylates, aromatic polyesters, and polyimides.

Mesh sheet 12 may comprise a single layer of material, or it may comprise two or more layers of material. Separate layers of material may or may not be co-extensive in length and/or width. Mesh sheet 12 may be at least partially woven or knitted. In some embodiments, mesh sheet 12 may have a pore size of from about 0.6 mm to about 1 mm, a thickness of about 0.5 mm to about 0.75 mm, and a tear resistance of greater than about 20 N. Other mesh sheets 12 with different physical properties are expressly contemplated.

Mesh sheet 12 may have a reinforcing material 14 in or on at least a portion of the mesh sheet 12. Reinforcing material may comprise any of a number of biocompatible materials, including but not limited to, synthetic composite materials such as polyglactin and/or poly p-dioxane undyed yarn. The reinforcing material can be applied to the mesh sheet 12 using any of a number of impregnating or application techniques. Reinforcing material 14 may be in the form of ribs or strips on at least a portion of the periphery of mesh sheet 12. Reinforcing material 14 may also be applied in the horizontal direction as a plurality of spaced apart rows. Although the strips of reinforcing material depicted in the drawings run the entire periphery of the reinforcing device 10 and include a plurality of spaced apart rows at a common length distance between adjacent rows, other configurations are contemplated.

In the embodiments of FIGS. 1 and 2, mesh sheet 12 also is equipped with two or more columns of hooks 16*a*, 16*b* that run parallel or substantially parallel to a longitudinal axis L of reinforcement device 10. The hooks depicted are shaped like inverted U's, which are similar to wickets used in croquet. Other shapes and configurations of hooks are contemplated; the hooks are structures through which suture may pass in sewing the reinforcement device 10 to the patient. These hooks 16*a*, 16*b* may be integrally formed with the mesh sheet 12 or added on or to the mesh sheet 12 using any of a number of methods. In the depicted embodiment, the common longitudinal distance between hooks within a spaced apart column is d1.

One or more of hooks 16*a*, 16*b* may also be affiliated with an aperture 17*a*, 17*b*. In the depicted embodiment, each of hooks 16*a*, 16*b* is affiliated with an aperture 17*a*, 17*b*. The apertures 17*a*, 17*b* are sized and shaped so that a marking end of a marking device may mark a patient's fascia where a needle and suture are to pierce a patient's fascia to attach the reinforcement device 10 to the patient. The ability to mark fascia may provide guidance in the form of a template to a surgeon for precision of location in a suturing process. Placement of apertures 17*a* and 17*b* is sufficiently distant from an incision point to avoid wound dehiscence.

In the depicted embodiment of FIGS. 1 and 2, the column with hooks 16*a* and the column with hooks 16*b* are on opposite sides of a longitudinal center region 18 that is substantially rectangular and encompasses center line 18'. Center region 18 falls between the spaced apart columns of hooks. Center region 18 extends from opposite ends of the mesh sheet 12, top edge to bottom edge. The top edge and bottom edge are opposite each other and are perpendicular to or substantially perpendicular to the longitudinal axis of mesh sheet 12. Within this center region 18, there is a reinforcing column of hooks 20. Hooks 20 may be of the same or a different material and/or configuration than the hooks 16*a*, 16*b*. Hooks 20 may be supported by reinforcing material 14. The longitudinal distance between hooks 20 is d2. In the depicted embodiment, d2 is greater than d1. Different configurations and variations between the length d1 and d2 are contemplated. For example, d2 may be 1.5× greater, 2× greater, 2.5× greater, 3× greater, 3.5× greater or 4× greater than d1. Different ratios may also be suitable.

Generally, reinforcement devices 10 may have a number of shapes and dimensions. In one non-limiting exemplary embodiment of a rectangular reinforcement device 10, a horizontal width of mesh sheet 12 is about 5 cm, a longitudinal length is about 15 cm or about 30 cm, d1 is about 1 cm, and d2 is about 3 cm. The length of reinforcement device 10 depends upon the length of incision, and a surgeon may cut a commercially available reinforcement device 10 to fit the size of a particular incision. The about 5 cm width overlap of the incision may add tensile strength to the wound to assist in reducing the incidence of incisional hernias. Generally, for about every 1 cm of d1 required to close a particular incision, about 4 cm of suture may be used. Stated another way, an exemplary ratio of suture length to wound length of 4 is one embodiment suited for prevention or reduction of incidence of incisional hernias. Different dimensions and different ratios are contemplated; those identified in this paragraph are merely exemplary teachings. A 4:1 ratio of length of suture length to incision length may be used. Substantially 4:1 may include variations such as 3.8:1 or 4.2:1, or other variations that fall from human application.

In the depicted embodiment of FIG. 3, one or more of the spaced apart columns of hooks and the reinforcing columns of hooks are eliminated from the reinforcement device 10. In this embodiment, there a plurality of spaced apart apertures arranged in columns. The depicted exemplary embodiment shows two columns of apertures left of a center line 18', and two columns of apertures right of the center line 18'. The outermost columns of apertures 30*a* and 30*b* (distal from the center line 18') are depicted as having a larger diameter than the innermost apertures 31*a* and 31*b* (proximal center line 18'). In one embodiment, the outermost apertures 30*a* and 30*b* have a diameter of about 2.5 mm, and the innermost apertures 31*a* and 31*b* have a diameter of about 1.3 mm. In one embodiment, the innermost apertures 31*a* and 31*b* are partially or fully reinforced to minimize or prevent tearing during suturing. The vertical distance between center points of the outermost apertures 30*a* may be about 5 mm, and the horizontal distance between center points of the outermost apertures 30*a* and 30*b* may be about 15 mm. The dimensions may vary and may be smaller or larger so long as for about every 1 cm of incision required to be closed, about 4 cm of suture may be used in connection with the reinforcement device 10.

Figure 4:
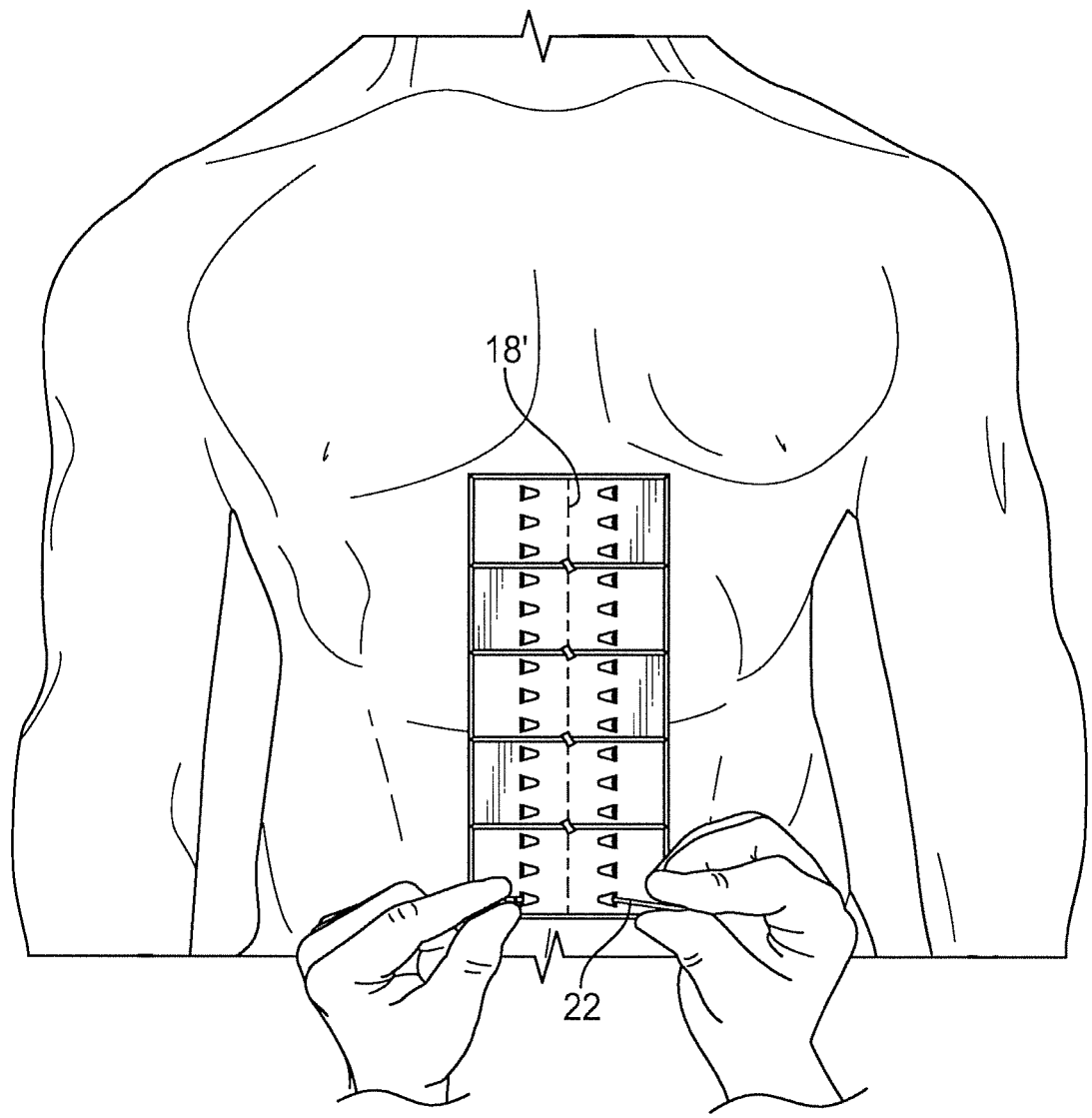
FIG. 4 is a top view of the exemplary reinforcement device of FIGS. 1 and 2 in connection with an abdomen of a patient.
Figure 5:
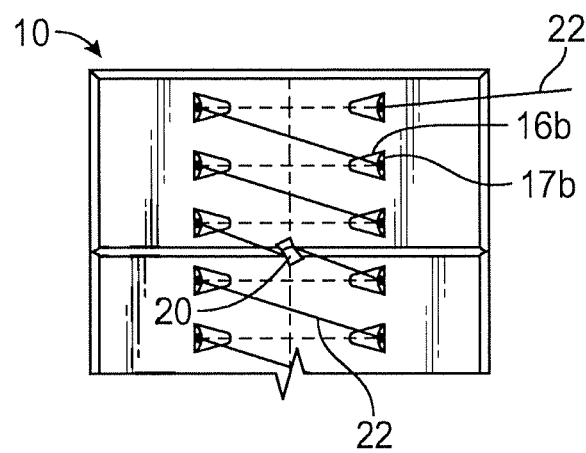
FIG. 5 is a perspective view of sutures connecting an exemplary reinforcement device to a patient through a plurality of hooks.
Figure 6:
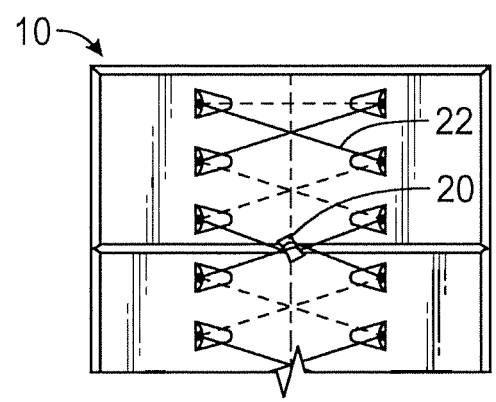
FIG. 6 is a perspective view of sutures connecting an exemplary reinforcement device to a patient through a plurality of hooks.

Referring to FIGS. 4-6, examples are shown where an exemplary reinforcement device 10 is used for closing and reinforcing an abdominal incision. The surgeon places the reinforcement device 10 over the fascia, attempting to align the center region 18, and the center line 18' with the incision itself. The surgeon may then mark a patient's fascia through the apertures 17*a* and 17*b* to indicate where the needle and suture are to pierce fascia to contemporaneously close the incision and sew the reinforcement device 10 to the patient. The device may be used in lieu of, for example, staples closing an incision. In one non-limiting embodiment, the apertures 17*a* and 17*b* are about 1 cm in horizontal distance from the center line 18'. If using an exemplary embodiment as shown in FIG. 3, such marking of the fascia may be performed through apertures 30*a* and 30*b*.

Figure 7:
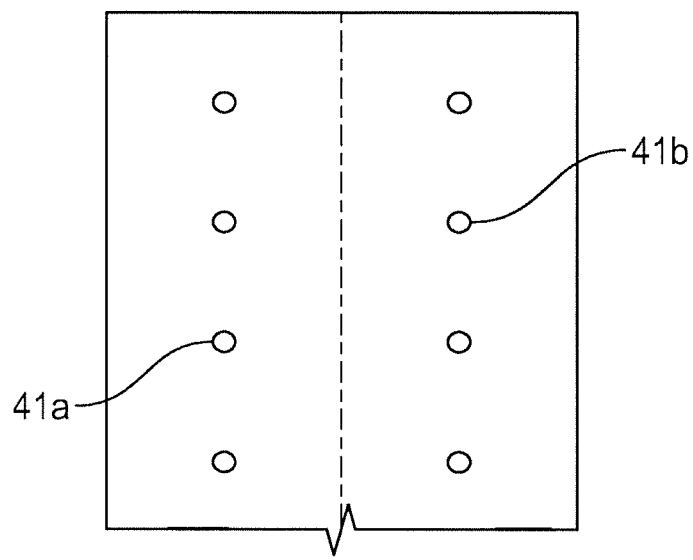
FIG. 7 is a top view of an exemplary reinforcement device.

Referring to FIG. 7, additional reinforcement devices 10 are shown. In one embodiment, reinforcement device 10 comprises a sheet 12 of biocompatible mesh having two columns of apertures 41*a* and 41*b*. For large abdominal incisions, the mesh sheet 12 may run 30 cm along a longitudinal axis and 5 cm across a latitudinal axis.

The apertures 41*a* and 41*b* may optionally be reinforced to minimize or prevent tearing during suturing. In one embodiment, longitudinal distance between apertures 41*a* in a column is about 0.5 cm. Lateral distance between a 41*a* aperture and a 41*b* aperture in the depicted embodiment is about 2 cm. Also in the depicted embodiment, the line formed between the each of the pairs of apertures 41*a* and 41*b* is parallel to the latitudinal axis. Alternative dimensions and configurations are contemplated, so long as the amount of suture 22 used to close an incision is about 3.8 to 4.2 times the length of the incision. In the depicted embodiment, there is a 4:1 ratio between suture length and incision length.

Figure 8:
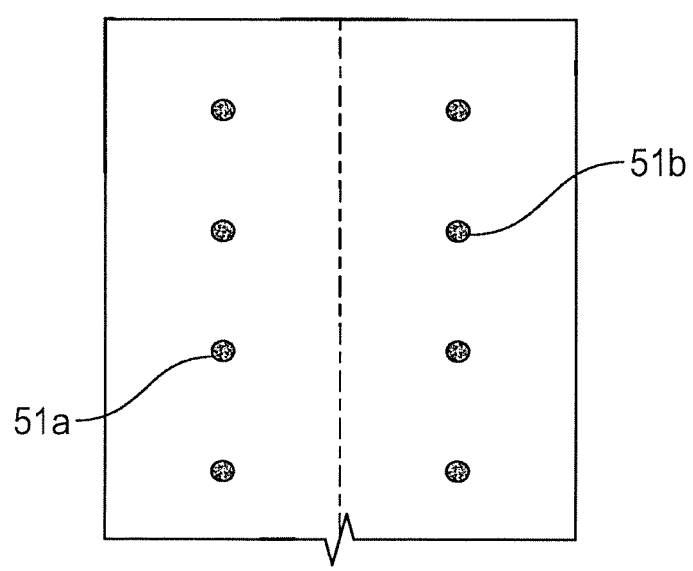
FIG. 8 is a top view of an exemplary reinforcement device.

Referring to FIG. 8, additional reinforcement devices 10 are shown. In one embodiment, reinforcement device 10 comprises a sheet of biocompatible mesh having two columns of markings 51*a* and 51*b*. For large abdominal incisions, the mesh sheet may run 30 cm along a longitudinal axis and 5 cm across a latitudinal axis.

The markings 51a and 51b indicate to a surgeon where to suture. In one embodiment, longitudinal distance between markings 51a in a column is about 0.5 cm. Lateral distance between a 51a marking and a 51b marking in the depicted embodiment is about 2 cm. Also in the depicted embodiment, the line formed between each of the pairs of markings 51a and 51b is parallel to the latitudinal axis. Alternative configurations are contemplated, so long as the amount of suture 22 used to close an incision is about 3.8 to 4.2 times the length of the incision. In the depicted embodiment, there is a 4:1 ratio between suture length and incision length.

The embodiment of FIG. 8 may simplify manufacturing procedures, minimize cost and complexity, and reduce or prevent any tearing of the biocompatible material during suturing.

Figure 9:
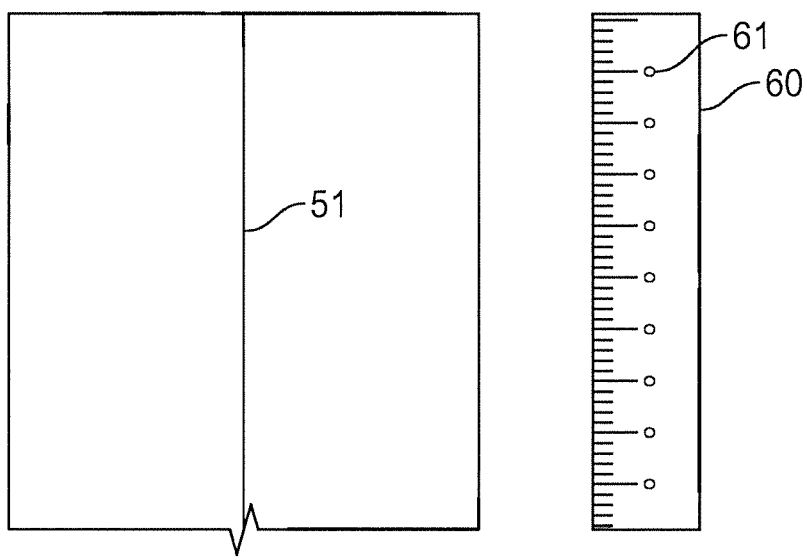
FIG. 9 illustrates exemplary contents of a surgical kit.

Referring to FIG. 9, an exemplary kit is shown with reinforcement device 10 and marking aid 60. One way to use the kit is to use the marking aid 60 to identify measured locations to mark fascia where sutures will enter and exit on both sides of an incision. The reinforcement device 10 can be used with marking aid 60 to align and position the marks so that the reinforcement device can be used to close and reinforce the incision. The amount of suture 22 used to close an incision is about 3.8 to 4.2 times the length of the incision. In the depicted embodiment, there is a 4:1 ratio between suture length and incision length.

In the depicted exemplary embodiment, device 10 is a mesh sheet 12 with a marked line 51 running along its center, with no holes other than the pores in the mesh. The line 51 may be used a locator, to be placed over the incision when the device 10 is used to close the incision and fasten the device 10 to fascia. The line 51 may run the entire length of the device 10, or it may run substantially the length of the device. The line 51 may be solid or dashed or dotted, so long as it is useful as a locator.

Using a center line 51 rather than marking the reinforcement device 10 with locations where a suture may enter and exit may reduce any confusion that may be caused if a marking position is missed on the mesh during manufacture due to the porous nature of the mesh.

Marking aid 60 may be a sterile, flexible ruler with markings in metric units. In one non-limiting embodiment, marking aid 60 includes a series of apertures 61 through which a device capable of marking fascia may be inserted. In one example, the marking aid 60 is one centimeter wide and includes apertures 61 every 0.5 cm along its longitudinal axis. Other iterations are possible. Marking aid 60 may be of any suitable material capable of providing guidance to a surgeon in marking fascia and aligning positions where suturing will occur in closing and reinforcing a wound.

The particular suture 22 and/or needle(s) (not shown) for use with the any of disclosed reinforcement devices 10 may be provided in a surgical kit including the reinforcement device 10, along with other medicaments, sterilizers, marking devices, cutting tools, instructions and other medical devices and equipment. Any of a number of commercially available sutures 22 may be used with the reinforcement device 10. The suture 22 may, for example, be bioabsorbable or non-bioabsorbable.

When the fascia is marked, a surgeon may position reinforcement device 10 in a position to commence suturing. Such position may be intra-peritoneal or extra-peritoneal, depending upon the materials of the reinforcement device 10. For example, bioabsorbable materials may be positioned to avoid potential for adhesion to internal organs. Generally, the suturing involves inserting the sutures 22 through the fascia, then looping the suture through hooks 16a to fascia to 16b to fascia to 16a to fascia to 16b, etc. in a series of generally Z-shaped formations or a series of generally X-shaped formations, possibly using a double needled suturing technique. Eventually, as a suturing pattern encounters a hook 20 in its general path, the surgeon may gain additional reinforcement by passing the suture 22 at least once through and/or around hook 20 before completing the connection between a hook 16a and a hook 16b. An exemplary non-limiting suturing pattern is indicated in FIG. 5, and another in FIG. 6. Other suturing patterns are contemplated.

Surgical placement of the reinforcement device 10 in a patient may be within the abdominal cavity if the materials making up reinforcement device 10 do not stick to organs. In another embodiment, surgical placement of the reinforcement device 10 may be beneath the fascia and above the peritoneum. In this surgical placement, when using an embodiment such as one as described in FIG. 3, both the apertures 30a, 30b and 31a, 31b may be useful. Markings may be performed through the distal apertures 31a and 30b, while sutures may be placed through the proximal apertures 31a and 31b. Surgical placement of the reinforcement device 10 in a patient may be above the fascia. In such a placement, the exemplary embodiment of FIG. 3 may be used where apertures are used to secure the device 10 in place.

With regard to the devices, kits, methods, etc. described herein, it should be understood that, although the steps of such methods, etc. have been described as occurring according to a certain ordered sequence, such methods could be practiced in an order other than the order described. It should also be understood that certain steps could be performed simultaneously, that other steps could be added, or that certain steps could be omitted.

The above description is intended to be illustrative, not restrictive. The scope of the invention should be determined with reference to the appended claims along with the full scope of equivalents. It is anticipated and intended that future developments will occur in the art, and that the disclosed devices, kits and methods will be incorporated into such future embodiments. Thus, the invention is capable of modification and variation and is limited only by the following claims.

What is claimed is:

1. A reinforcement device for reinforcing closures of abdominal surgical incisions, comprising:
   a biocompatible sheet;
   a plurality of markings arranged in spaced apart parallel columns on the sheet to indicate location for suturing, wherein the markings are spaced apart such that a length of suture for closing an incision according to the markings is configured to result in a ratio of suture length to incision length of from 3.8:1 to 4.2:1.

2. The reinforcement device of claim 1, wherein the markings are spaced apart such that a length of suture for closing an incision according to the markings is configured to result in a ratio of suture length to incision length of 4:1.

3. A surgical kit for reinforcing closures of an abdominal surgical incision, comprising:
   biocompatible mesh having a center line marked along its length;
   a marking aid with delineated distance markings configured for aligning and positioning marks where sutures enter and exit the mesh to close and reinforce an abdominal surgical incision such that the marks are configured to be indicative of a ratio of suture length used to close an incision to incision length that is from 3.8:1 to 4.2:1, wherein the marking aid includes a series of apertures for receiving a device capable of marking fascia surrounding the abdominal surgical incision.

4. The kit of claim 3 further comprising a device capable of marking the fascia.

5. The kit of claim 4 further comprising suture.

6. A reinforcement device for reinforcing closures of abdominal surgical incisions, comprising:
   a biocompatible sheet;
   a plurality of apertures arranged in spaced apart parallel columns on the sheet, the apertures being sized and shaped for passage of suture therethrough; and
   a length of suture for closing an incision, wherein the apertures are positioned such that the length of suture for closing the incision using the device is from 3.8 to 4.2 times greater than a length of the incision to be closed.

7. The reinforcement device of claim 6, wherein the apertures are reinforced.

8. The reinforcement device of claim 6, wherein the length of suture for closing an incision using the device is 4 times greater than a length of an incision to be closed.

9. A device for reinforcing a closure of an abdominal surgical incision, comprising:
   a mesh sheet having two spaced apart parallel columns of suture apertures sized and shaped for passage of suture through the mesh sheet, the mesh sheet being continuous and uninterrupted between the apertures of the two spaced apart parallel columns of apertures; and
   a length of suture, wherein the suture apertures are spaced such that for every 1 cm of length of an incision required to be closed about 4 cm of suture is provided to connect the device to the abdominal fascia.

10. The device of claim 9, wherein the two parallel columns of suture apertures are on opposite sides of a longitudinal center line of the mesh sheet.

11. The device of claim 10, further comprising third and fourth columns of marking apertures spaced on opposite sides of the center line of the mesh sheet and spaced further from the center line of the mesh sheet than the two columns of suture aperture, the marking apertures sized and shaped for marking abdominal fascia.

* * * * *